United States Patent [19]

White

[11] 4,021,478

[45] May 3, 1977

[54] PREPARATION OF CARBOXYLIC ACIDS FROM GLYCIDONITRILES WITH IONIC LEWIS ACIDS

[75] Inventor: David R. White, Kalamazoo, Mich.

[73] Assignee: The Upjohn Company, Kalamazoo, Mich.

[22] Filed: Apr. 23, 1976

[21] Appl. No.: 680,002

Related U.S. Application Data

[63] Continuation of Ser. No. 531,671, Dec. 10, 1974, abandoned, and a continuation-in-part of Ser. No. 271,389, July 13, 1972, abandoned.

[52] U.S. Cl. .................... 260/515 R; 260/239 BA; 260/287 R; 260/293.88; 260/295 R; 260/326.4; 260/326.11 R; 260/326.13 R; 260/332.2 A; 260/345.2; 260/345.7; 260/397.1; 260/413; 260/465 R; 260/465.1; 260/479 R; 260/488 R; 260/514 R; 260/514 H; 260/514 G; 260/514 L; 260/515 A; 260/515 P; 260/520 R; 260/521 R; 260/526 N; 260/534 R; 260/535 R; 260/539 R; 260/540

[51] Int. Cl.$^2$ ........................................ C07C 51/00

[58] Field of Search .......... 260/515 R, 540, 526 N, 260/514 R

[56] References Cited

OTHER PUBLICATIONS

Gerkin, (Univ. of California Thesis, 1968), Available through Univ. Microfilms, Inc., Ann Arbor, Mich., Order No. 70-2065, pp. 15–20, 38–43, 54, 55, 94–96, 154, 155, 194, 195, 197, 203 & 204.

McDonold et al., J. Org. Chem., 35, pp. 2942–2947 (1970).

March, "Advanced Organic Chemistry: Reactions, Mechanisms and Structure," p. 288 (1968).

Thyagarajan, "Mechanisms of Molecular Migrations," vol. 3, pp. 91–96 (3–30–71).

Hine, "Physical Organic Chemistry," 2nd Ed., p. 161.

Petty, J. Am. Chem. Soc., 76, pp. 4385–4389, (9–5–74).

*Primary Examiner*—Lorraine A. Weinberger
*Assistant Examiner*—Michael Shippen
*Attorney, Agent, or Firm*—John T. Reynolds

[57] ABSTRACT

Process for preparing carboxylic acids by converting a glycidonitrile to a 2-oxopropionitrile via use of an ionic Lewis acid, and conversion of the 2-oxopropionitrile to the carboxylate salt with a base and of the salt to the carboxylic acid with acid.

The process is especially useful for the preparation of 2-(p-isobutylphenyl)propionic acid, (Ibuprofen), also known as Motrin, a known and highly active antiinflammatory agent as well as a host of other carboxylic acids which are known in the art as useful compounds.

4 Claims, No Drawings

PREPARATION OF CARBOXYLIC ACIDS FROM GLYCIDONITRILES WITH IONIC LEWIS ACIDS

CROSS REFERENCE

This is a continuation of application Ser. No. 531,671, filed Dec. 10, 1974, now abandoned; which is a continuation-in-part to application Ser. No. 271,389, filed July 13, 1972, now abandoned.

BACKGROUND OF THE INVENTION

Prior art carboxylic acid syntheses from aromatic ketones by the addition of hydrogen cyanide such as disclosed by Eliel et al. Org. Syn. 33, 7 (1953) involve a reversible step with an unfavorable equilibrum as well as a reduction step. In the process of the present invention the steps are irreversible and no reduction step is required. The process of the present invention thus results in greatly increased yields and higher purity of the desired carboxylic acid. The carboxylic acids which can be produced by the process of this invention are known in the art as useful compounds. For example, 2-(p-isobutylphenyl)propionic acid and 2-(m-fluoro-p-phenyl)phenylpropionic acid are highly active antiinflammatory agents, and 3,4-dimethyoxyphenylacetic acid is useful in preparing papaverine.

SUMMARY OF THE INVENTION

The novel process of this invention is illustratively represented by the following reaction sequence:

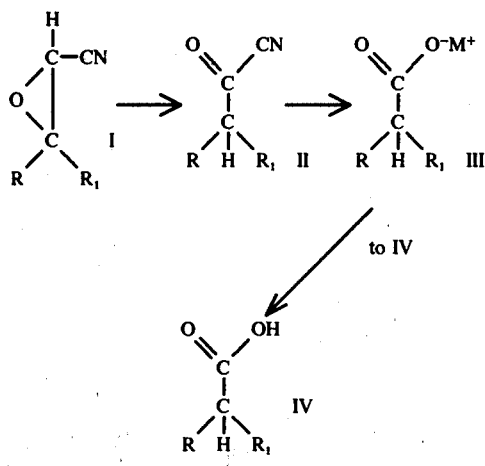

wherein in the above formulae when taken separately R represents hydrogen, an aliphatic, alicyclic, aromatic or heterocyclic group and $R_1$ when taken separately represents an aliphatic, alicyclic, aromatic or heterocyclic group; R and $R_1$ when taken together and connected represent an alicyclic or heterocyclic group, $M^+$ is an alkali metal selected from the group consisting of sodium, potassium and lithium.

Included among the aliphatic, alicyclic and aromatic groups which R and $R_1$ can each represent when taken separately are, for example, alkyl (including saturated and unsaturated, straight and branched chain alkyl and cycloalkyl) and aryl (including alkaryl and aralkyl) radicals, such as methyl, ethyl, propyl, isopropyl, n-butyl, sec. butyl, tert. butyl, amyl, hexyl, heptyl, octyl, decyl, dodecyl, octadecyl, vinyl, allyl, methallyl, butenyl pentenyl, hexenyl, heptenyl, octenyl, ethynyl, propynyl, butynyl, pentynyl hexynyl, heptynyl, octynyl and isomeric thereof, cyclobutyl, cyclopentyl, cyclohexyl, 1-cyclohexenyl, methylcyclohexyl, cycloheptyl, cyclooctyl, cyclodecyl, cycloundecyl, cyclododecyl, cyclopentadecyl, phenyl, tolyl, xylyl, benzyl, phenethyl, phenylpropyl, benzhydryl, 1- and 2-naphthyl, naphthylmethyl, o-carboxylbenzyl, and the like, as well as fused and briged ring structures, such as indanyl, indenyl, naphthyl, acenaphtyl, phenanthryl, cyclopentanopolyhydrophenanthryl, adamantacyl, bicyclo[3:1:1]heptyl, bicyclo[2:2:2]octyl and the like; all of which can either be unsubstituted or substituted with one or more non-interfering substituents, such as hydroxyl derivatives, for example, alkoxy such as methoxy, ethoxy, propoxy, butoxy, and the like; acyloxy, such as acetoxy, propionoxy, butyroxy and the like nitro groups; amino groups; alkylamino groups, such as methylamino, ethylamino, dimethylamino and the like; halogens, such as fluorine, chlorine, or bromine; carbonyl derivatives such as enol ethers and ketals; and the like.

Included among the heterocyclic groups which R and $R_1$ can represent are substituted and unsubstituted azabicycloalkane groups such as azabicyclo[3:2:2]octyl and azabicyclo[3:2:1]nonyl and the like, furfuryl groups, tetrahydrofurfuryl groups, piperidyl groups, pyrrolidyl groups, pyridyl groups, thiophene groups, alkaloid nuclei groupings containing for example indole, dihydroindole, quinolidine, quinthio groups and the like.

Included among the alicyclic and heterocyclic groups which $R_1$ and $R_2$ when taken together and connected can represent, are cyclopropyl, cyclobutyl, cyclohexyl, dicyclohexyl, cyclodecyl, cyclododecyl, cyclopentadecyl, and the like, piperidyl, pyrrolidyl, and the like; fused ring systems such as cyclopentanopolyhydrophenanthranyl, indanyl, indenyl, and the like, bridged ring systems such as adamantyl, bicyclo[2:2:1]heptyl, bicyclo[2:2:2]octyl, bicyclo[3:2:2]nonyl, azabicycloalkyls, and the like, all of which can be substituted by non-interfering substituents such as those hereinbefore named.

The compounds of formula II, above, are known to dimerize under certain conditions as shown by the following sequence of formulae:

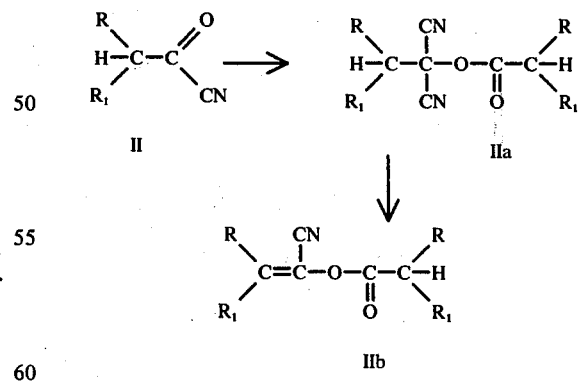

wherein R and $R_1$ have the same meanings given above. For simplicity the compounds of formula II will be referred to in terms of their monomeric structure (II). For the purpose of this invention, their particular structure is not important since all forms react in the subsequent process steps to produce the desired carboxylic acids (IV).

DETAILED DESCRIPTION OF THE INVENTION

The starting glycidonitriles of formula I are either known in the art or can be prepared from known ketones and aldehydes by a Darzens condensation, for example in accordance with the procedure disclosed by V. F. Martynov and A. V. Schelkunov, J. Gen. Chem. USSR 27, 1271-3 (1957). In preparing the necessary starting materials, a ketone or aldehyde of formula VII;

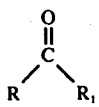
VII wherein R and $R_1$ have the same meanings given above is reacted with chloroacetonitrile in the presence of a strong base such as sodium methoxide, potassium t-butoxide, sodium t-amylate and the like. The reaction is carried out in a non-polar aprotic solvent such as xylene, toluene, hexanes, petroleum ethers and the like, preferably at a relatively low temperature, such as from about −10 to about +10° c., for a period of from about 1 to 5 hours. In our preferred operation of this step we use sodium hydroxide in a mixture of dimethylformanide and toluene. The glycidonitrile (I) thus obtained is recovered and can be purified by conventional methods, for example, by distillation under reduced pressure, but we prefer not to purify it.

In carrying out the process of this invention, the glycidonitrile of formula I are subjected to the following reaction steps:

The selected glycidonitrile (I) is dissolved or suspended in a suitable inert organic solvent, for example, hexanes, petroleum ethers, diethylether, xylene, toluene and the like, relatively high boiling solvents such as xylene, toluene, high boiling petroleum ethers, e.g., Skellysolve V, and the like or mixtures thereof, are advantageous. The solution thus obtained is then treated with a Lewis acid which has a non-nucleophillic anion, i.e., an ionic Lewis acid such as potassium bisulfate, lithium trifluoroacetate, lithium perchlorate, lithium, tetrafluoroborate, lithium sulfate, and the like. Lithium perchlorate is preferred. The time required for rearrangement of the glycidonitriles of formula I to obtain the corresponding 2-oxopropionitrile of formula II is dependent in part on the temperature at which the reaction is carried out, a temperature between about 100° C. to about 160° C. is preferably employed (reflux temperature is advantageous) for a period of from about a few minutes to about 24 hours for completion of the reaction. For example, at 110° C. about 16 to 24 hours are required whereas at 140° C. 3 to 4 hours is generally sufficient for completion of the reaction. The compounds of formula II thus obtained can be recovered from the reaction mixture and purified by conventional methods, for example, chromatography and/or crystallization from a suitable solvent such as methylene chloride, ethylacetate, xylene, toluene, hexanes, benzene and the like or by distillation under reduced pressure. Alternatively, the compounds of formula II are used directly in the next step without recovery from the reaction medium.

The compounds of formula II thus obtained are then subject to hydrolysis under the basic conditions, preferably in the presence of an alkali metal base such as sodium hydroxide, potassium hydroxide, lithium hydroxide, sodium carbonate, potassium bicarbonate and the like to give the alkali metal salt of the corresponding carboxylic acid (III). The hydrolysis is carried out within a broad temperature range, for example from about 0° C. to about 00° C., for a period of from about 1 to about 24 hours, however, temperature within the range of from about 40 to 80° C. are preferred. The carboxylic acid salt (III) thus obtained is recovered and purified by conventional methods or the salt is used in the next step without purification. When the sodium salt (III) is a solid, it is often advantageous to recover the salt from the reaction mixture by crystallization prior to acidification since it results in higher purity of the desired free carboxylic acid (IV).

The sodium salt (III) thus obtained is then subjected to acidification with a strong acid, for example, hydrochloric acid, sulfuric acid, phosphoric acid, trifluoroacetic acid, p-toluenesulfonic acid, benzenesulfonic acid, methanesulfonic acid and the like, to obtain the corresponding free acid (IV). The acidification is carried out within a broad temperature range such as from about 0° C. or lower to the boiling point to the reaction mixture. The product (IV), thus obtained, is recovered from the reaction mixture and purified by conventional methods, for example, the product is extracted from the reaction mixture in a suitable organic solvent such as Skellysolve B hexanes, toluene, xylene, ethyl acetate, benzene, methylene chloride, chloroform and the like and crystallized, if the product is a solid. If the product is a liquid it is recovered and purified by distillation, preferably at reduced pressure.

None of the intermediates need to be isolated and purified. The entire process can be conveniently carried out in a one pot operation.

The following Preparations and Examples illustrate the best mode contemplated for carrying out the invention, but are not to be construed as limiting the scope thereof.

PREPARATION A

A mixture of 17.6 g. of p-isobutylacetophenone (VII) and 61 ml. of a 15.4% w/v solution of chloroacetonitrile in xylene is cooled to about −10° C. and a solution of sodium t-amylate (prepared by stirring 4.45 g. of sodium amide and 10.0 g. of t-amyl alcohol in 150 ml. of xylene at 60° C. for about 4 hours) is added with stirring over a period of about 15 minutes keeping the temperature at about −5° C. (we now prefer to use flake sodium hydroxide in a dimethylformamide/toluene mixture for this step.) Stirring is continued for an additional period of about 1 hour and then 70 ml. of water is added. The reaction mixture is then filtered and the organic (xylene) phase is separated. The aqueous layer is extracted with 30 ml. of xylene and the xylene solutions are combined, dried over anhydrous sodium sulfate and concentrated. The residue thus obtained is distilled (105° C./.05 mm.) to give 18.88 g. (88% yield) of 3-methyl-3-(p-isobutylphenyl)-glyciconitrile (I) as an oil. However, distilling is not necessary.

Example 1 2-(p-isobutylphenyl)propionic acid (IV)

A solution of 3-methyl-3-(p-isobutylphenyl)-glycidonitrile (I) about 60% in toluene, obtained from 0.050 mole of p-isobutylacetophenone (99.5% yield) in accordance with the procedure described in Preparation A, above, is diluted with 10 ml. of Skellysolve V petroleum ether and treated with 0.400 g. of lithium perchlorate. The mixture is heated with stirring under nitrogen in a 115° C. oil bath for about 25 hours (reaction time at 122° C. about 17 hours) to give 3-methyl-3-(p-isobutylphenyl)-2-oxopropionitrile (II). The reaction mixture is cooled to about 70° C., diluted with 30 ml. of toluene and 10 ml. of water, treated with 8.0 ml. of aqueous, 50% sodium hydroxide and then 60 mg. of catalin is added and the mixture stirred at 75° C. for 4 hours. The reaction is diluted with 15 ml. of acetone and cooled to about 0° C. with stirring. The crystalline salt thus obtained is collected on a filter, washed with toluene and then with cold acetone to give the sodium salt of 2-(p-isobutylphenyl)propionic acid (IV).

The sodium salt thus obtained is then taken up in 70 ml. of Skellysolve B hexanes and 20 ml. of water and then 10 ml. of 12 N sulfuric acid is added with stirring. The two phases are then separated and the organic (upper) phase is washed with warm water. The combined aqueous phase is washed again with 20 ml. of Skellysolve B hexanes which is backwashed with 20 ml. of water. The organic phases are combined, dried over anhydrous sodium sulfate, concentrated to about 18 ml. and allowed to crystallize. The solid thus obtained is collected on a filter and washed with cold Skellysolve B hexanes to give 7.42 g. (72% yield) of 2-(p-isobutylphenyl)propionic acid (IV); m.p. 73°–74.1° C.; λmax (CH$_3$OH) 263 and 272mg; IR and NMR spectra support the assigned structure.

Following the procedure of Preparation A and Example 1, above, other glycidonitriles of formula (I) can be converted to the corresponding carboxylic acids of formula (IV). The following conversions are representative:

3,4-dihydrospiro[naphthalene-1(2H),2′-oxirane]-3′-carbonitrile to obtain 1,2,3,4-tetrahydro-1-naphthoic acid, 17β-acetoxyspiro[androstane-3,2′-oxirane]-3′-carbonitrile to obtain 17β-acetoxyandrostane-3β-carboxylic acid, spiro[adamantane-2,2′-oxirane]-3′-carbonitrile to obtain 2-adamantanecarboxylic acid, β-phenylcylohexaneglycidic acid to obtain α-phenylcyclohexaneacetic acid, 3,3-diphenylglycidic acid to obtain diphenylacetic acid, 1,2,3,4-tetrahydrospiro[anthracene-9(10H),2′-oxirane]-3′-carbonitrile to obtain 1,2,3,4,9,10-hexahydro-9-anthroic acid, tetrahydrospiro[oxirane-2,4′-[4H]pyran]-3-carbonitrile to obtain tetrahydro-4H-pyran-4-carboxylic acid, and spiro[1H-2-benzopyran-4(3H),2′-oxirane]-3′-carbonitrile to obtain 3,4-dihydro-1H-2-benzopyran-4-carboxylic acid.

Example 2 2-(p-isobutylphenyl)propionic acid (IV)

Following the procedure of Example 1, above, but substituting a stoichiomeric equivalent amount of fused potassium bisulfate in place of lithium perchlorate gives 2.31 g. (22.4% yield) of 2-(p-isobutylphenyl)propionic acid (IV).

Example 3 2-(m-fluoro-p-phenyl)phenylpropionic acid

Following the procedure of Preparation A, above, but substituting a stoichiometric equivalent amount of m-fluoro-p-phenylacetophenone (VII) as starting material in place of p-isobutylacetophenone gives 2-methyl-2-(m-fluoro-p-phenyl)phenylglycidonitrile (I) which is converted by the procedure of either Example 1 or 2 to obtain 2-(m-fluoro-p-phenyl)phenylpropionic acid (IV).

Example 5 cyclopentanecarboxylic acid

Following generally the procedure of Example 1, 7.80 g. (0.06 mole) of the crude glycidonitrile of cyclopentanone in 9.0 ml. of toluene was reacted with 0.30 g. of lithium perchlorate to form the 1-cyclopentyl 1-oxo-acetonitrile.

The nitrile containing reaction mixture was treated with 6.0 ml. of aqueous 50 percent sodium hydroxide solution in a mixture of 18 ml. of toluene and 9.0 ml. of water and stirred at 80° C. overnight. The resulting reaction mixture was diluted with 75 ml. of water and phase were separated. The organic layer phase was washed with 20 ml. of 1N aqueous sodium hydroxide and the resulting aqueous phase was separated from the organic phase and combined with the original aqueous phase. The resulting aqueous phase was washed with 30 ml. of toluene and then acidified with 15 ml. of 12N sulfuric acid and extracted twice with 100 ml. portions of ethyl acetate. The ethyl acetate extracts were combined, washed with 30 ml. of water, and dried over sodium sulfate, and concentrated to 3.0 g. of a thick brown oil. This oil was distilled to obtain two fractions (1) 314 mg., b.p. 105°–110° C. and (2) 846 mg., b.p., 110°–115° C. (total 1.16 g., 17% yield), of cyclopentanecarboxylic acid, which was confirmed by infrared spectrum analysis.

In the acid production process of this invention the glycidonitrile is reacted in the first step with an ionic Lewis acid which converts the glycidonitrile to a substituted 2-oxopropionitrile, which propionitrile is then converted to the salt with strong base, and the salt is hydrolyzed to the acid, without rearrangement of the substituents or the carbon skeleton. Thus, for example, when the process is applied to the production of 2-(p-isobutylphenyl)propionic acid the arrangement of the substituents on the carbon atom skeleton involved in the reaction can be illustrated as follows:

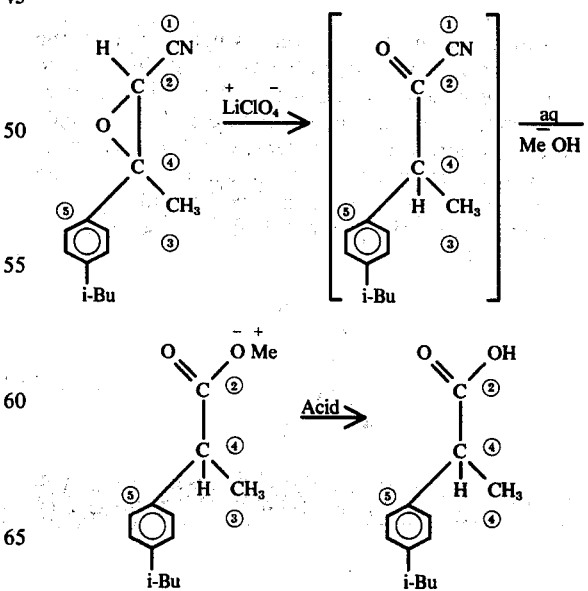

wherein i-Bu denotes the isobutyl group on the phenyl substituent and Me⁺ denotes the cation from the strong base. In preparing the final carboxylic acid product the cyano carbon is expelled and carbon②in each molecule remains attached to the unchanged carbon skeleton chain③,④and⑤at carbon④throughout the process. In other words, carbons②,③,④ and ⑤ which survive in the product do not change their relative positions. The brackets around the formula of the product of the first ionic Lewis acid reaction indicate that the product therein is hypothetical; at least in our work that bracketed product exists as a mixture of two dimers

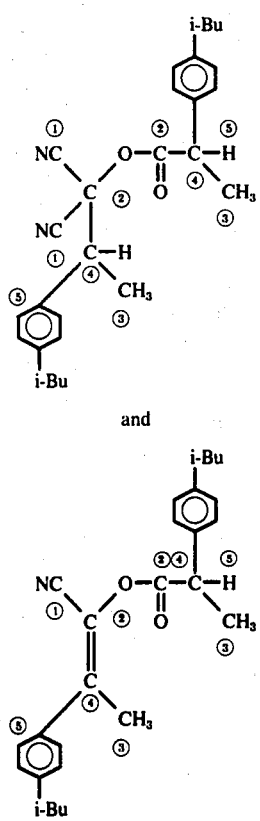

and

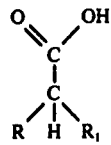

but even in the dimers all atoms which appear in the final acid product remain on the carbon skeleton chain 3, 4 5 in the same relative position. This process offers the advantage of being able to prepare carboxylic acids from glycidonitriles in three steps, which process does not effect a rearrangement of the substituents on the carbon atom skeleton of the carboxylic acid.

1. A process for the production of a carboxylic acid of the formula:

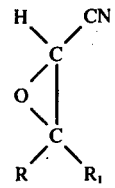

wherein R when taken separately represents hydrogen or an aliphatic, alicyclic, aromatic or heterocyclic group and $R_1$ when taken separately represents an aliphatic, alicyclic, aromatic or heterocyclic group; and R and $R_1$ when taken together and connected represents an alicyclic or heterocyclic group, which comprises:

1. treating a glycidonitrile of the formula:

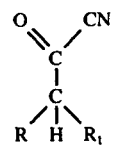

wherein R and $R_1$ have the meanings given, above, with an ionic Lewis acid selected from the group consisting of lithium perchlorate, lithium trifluoroacetate, lithium tetrafluoroborate, lithium sulfate or potassium bisulfate to obtain a 2-oxopropionitrile of the formula:

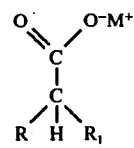

wherein R and $R_1$ have the meanings given, above;

2. subjecting the 2-oxopropionitrile so obtained to hydrolysis with an aqueous alkali metal base to obtain an alkali metal salt of a carboxylic acid of the formula:

$$\underset{R\ H\ R_1}{\overset{O}{\underset{\|}{C}}-\overset{}{\underset{|}{C}}-O^-M^+}$$

wherein R and $R_1$ have the meanings given, above, and M⁺ is selected from the group consisting of sodium, potassium and lithium, and 3. acidifying the alkali metal salt of the carboxylic acid so obtained with a strong acid to obtain the corresponding free carboxylic acid.

2. The process in accordance with claim 1, wherein the Lewis acid is lithium perchlorate.

3. The process in accordance with claim 1 for the production of 2-(p-isobutylphenyl)propionic acid, wherein the starting glycidonitrile is 3-methyl-3-(p-isobutylphenyl)glycidonitrile.

4. The process for the production of 2-(p-isobutylphenyl)-propionic acid which comprises:
   1. treating 3-methyl-3-(p-isobutylphenyl)glycidonitrile with lithium perchlorate;
   2. subjecting the 3-methyl-3-(p-isobutylphenyl-2-oxopropionitrile thus obtained to hydrolysis with an aqueous alkali metal base to obtain the corresponding alkali metal salt of 2-(p-isobutylphenyl)-propionic acid; and
   3. acidifying the salt thus obtained with a strong acid to obtain 2-(p-isobutylphenyl)propionic acid.

* * * * *